United States Patent [19]

Nesmeyanov et al.

[11] 3,984,567

[45] Oct. 5, 1976

[54] METHOD OF TREATING OZENA

[76] Inventors: Alexander Nikolaevich Nesmeyanov, Glavnoe zdanie MGU, korpus "K", kv. 105, Moscow; Ljubov Grigorievna Bogomolova, ulitsa Nekrasova, 60, kv. 131, Leningrad; Nadezhda Sergeevna Kochetkova, ulitsa Garibaldi, 23/56, korpus 4, kv. 27, Moscow; Vera Dmitrievna Vilchevskaya, ulitsa Dmitria Ulyanova, 4, korpus 2, kv. 47, Moscow; Nikanor Petrovich Palitsyn, ulitsa Stankevicha, 12, kv. 10, Moscow; Julia Julievna Gorelikova, Nagatinskaya ulitsa, 58, korpus 2, kv. 73, Moscow; Irina Gennadievna Andrianova, prospekt Smirnova, 43, kv. 27, Leningrad; Olga Petrovna Belozerova, prospekt Mira, 124, korpus 15, kv. 72; Vera Khusainovna Sjundjukova, ulitsa Vavilova, 44/2, kv. 154, both of Moscow, all of U.S.S.R.

[22] Filed: May 22, 1975

[21] Appl. No.: 579,803

Related U.S. Application Data

[63] Continuation-in-part of Ser. No. 423,533, Dec. 10, 1973, abandoned, which is a continuation of Ser. No. 119,356, Feb. 26, 1971, abandoned.

[52] U.S. Cl. .............................................. 424/295

[51] Int. Cl.$^2$........................................ A61K 31/295
[58] Field of Search .................................... 424/295

[56] References Cited
UNITED STATES PATENTS

| | | | |
|---|---|---|---|
| 3,035,978 | 5/1962 | Jones et al. | 424/295 |
| 3,099,699 | 7/1963 | Leigh | 424/295 |

OTHER PUBLICATIONS

Derwent Publication Abstracting USSR 179,309 published 8/1966.
Merck Manual 12th Edition (1972) pp. 255–257, 952, 968–972.
Stedman's Medical Dictionary, 21 Edition 1969 pp. 1158, 1181, 1205.
Goodman et al., The Pharmacological Basis of Therapeutics (1966) pp. 1403–1406.

*Primary Examiner*—Norman A. Drezin
*Attorney, Agent, or Firm*—Haseltine, Lake & Waters

[57] ABSTRACT

The medicinal preparation for treating ozena comprises an active ingredient, viz. the sodium salt of o-carboxybenzoylferrocene, combined with a pharmaceutical filler for tablets.

The method of treating ozena in humans comprises oral administration of tablets containing from 0.1 to 0.3 g of the active ingredient, viz., the sodium salt of o-carboxybenzoylferrocene, 2 or 3 times a day for 20 to 40 days.

2 Claims, No Drawings

METHOD OF TREATING OZENA

The present application is a continuation-in-part of Serial No. 423,533 filed Dec. 10, 1973 which was a continuation of Ser. No, 119,356, filed Feb. 26, 1971, both now abandoned.

The present invention relates to a novel medicinal preparation for treating ozena and to a method of treating ozena in humans.

In accordance with the invention, the proposed medicinal preparation for treating ozena comprises an active ingredient viz., the sodium salt of o-carboxybenzoylferrocene, of the following formula

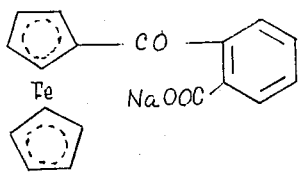

and a pharmaceutical filler for tablets.

The active ingredient of the proposed preparation, viz., the sodium salt of o-carboxybenzoylferrocene, is a dark-orange bitter crystalline powder soluble in water and stable on exposure to air.

Ozena is an extremely grave disease which is very difficult to treat. It is known in the art to employ a variety of therapeutic strategies, both medicamentous and surgical. The former are based on the use of Bogomolets' antireticular cytotoxic serum, lysates, aeronization combined with direct transfusion of Academician Filatov's aeronized serum, salts of heavy metals, streptomycin emulsion, nicotinic acid combined with streptomycin and vitamin A, etc.

Of the surgical methods of treatment of ozena, the following merit attention: multiple-stage cadaveric cartilage transplantation, amnion implantation, placenta grafting and grafting of polymers.

All these methods are instrumental in effecting a temporary improvement, but not sustained effect. The medicamentous course of therapy is preferable to surgery as involving no risk of trauma.

In accordance with the invention, the proposed method of treatment of ozena in humans comprises oral administration of tablets containing 0.1 to 0.3 g of the active ingredient, viz. the sodium salt of o-carboxybenzoylferrocene, 2 or 3 times a day for 20 to 40 days.

The proposed preparation was subjected to clinical trials on 100 ozena patients all of whom displayed a typical form of the disease: wide nasal passages, crusts with a pungent offensive odor, pronounced atrophy of the nasal mucosa and the bony framework of the turbinated bones and a dramatic deterioration of the sense of smell. By age and sex, the patients were classified as follows: 15 men and 85 women; 64 patients were aged from 8 to 20.

Prior to the therapy, all the patients were subjected to a comprehensive clinical examination including a clinical blood test, erythrocyte sedimentation rate determination, X-ray inspection of the paranasal sinuses, Wassermann test, urine test and blood serum iron determination by the phenanthroline method according to Balakovsky.

The clinical blood test, ESR, urine test and other analyses were found to be normal in all patients; furthermore, the tests showed no symptoms typical of anemia (erythrocyte count and hemoglobin were normal), just as there were no other clinical symptoms of anemia such as brittleness of the nails, giddiness, general weakness, palpitation of the heart, loss of appetite, etc.

Prior to the therapy, it was histologically found that the tissues of the nasal mucosa showed an iron deficiency. For this reason the ozena patients were studied for iron metabolism in the blood serum prior to and following the course of treatment with the proposed preparation.

All patients were found, before the therapy began to have a reduced level of iron in the blood serum: from 0.06 to 0.11 mg% (the normal level being 0.25 mg%).

All these patients were treated with the proposed medicinal preparation containing from 0.1 to 0.3 g of the active ingredient, viz. the sodium salt of o-carboxybenzoylferrocene. The patients received 2 or 3 tablets a day for 20 to 30 days. Depending on the clinical effect and biochemical analyses, some patients received a 40-day course of said therapy.

Following the therapy, all the patients registered a rise of blood-serum iron to 0.28 to 0.35 mg% accompanied by a pronounced clinical improvement: the secretary functions improved, the crusts disappeared and the offensive odor was gone; the olfactory function also underwent a marked improvement in most patients so that they could distinguish between various smells. No diet was prescribed in the course of the therapy. The tablets were chased with water alone.

Blood-serum iron tests taken 3 or 4 months later demonstrated that said method of treatment had a high therapeutic effect, as the level of iron had risen to 0.43 mg%. In a more remote period, 1.5 to 2 years after the therapy, the blood-serum iron of some patients dropped to as low as 0.12 mg%. The latter patients were given a repeated course of treatment with satisfactory clinical results. No concomitant therapy was given.

The proposed preparation is used in tablet form.

In accordance with the invention, the preferred pharmaceutical filler is confectioner's sugar or starch. The preferred content of the active ingredient, viz., the sodium salt of o-carboxybenzoylferrocene, in one tablet is from 0.1 to 0.3 g.

The proposed medicinal preparation is manufactured by a known method. The active ingredient of the proposed preparation, viz., the sodium of o-carboxybenzoylferrocene, is preferably produced by the following route: An apparatus equipped with a heating jacket, a reflux condenser and stirrer is charged with phthalic anhydride and absolute ethanol, and the resultant mixture is heated with stirring at the alcohol boiling point until all phthalic anhydride has been completely dissolved. The heating is continued for another 30 minutes and the alcohol residue is distilled off in vacuum at a temperature not exceeding 50°C:

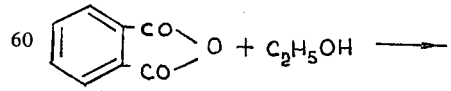

Thionyl chloride is added to the resultant residue by small portions:

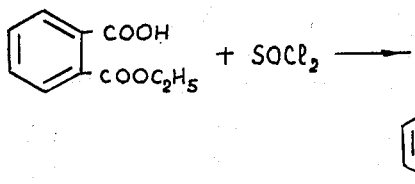
+ SOCl$_2$ →

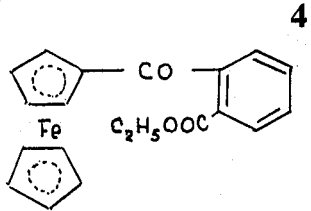
+ NaOH →

The reaction mixture thus obtained is heated for an hour at a temperature of 35°C and stirred.

The excess thionyl chloride and the by-products of the reaction are distilled off in vacuum at a temperature not exceeding 50°C.

To the obtained monoethyl o-phthalate chloride is added methylene chloride as solvent and ferrocene with stirring and passing in inert gas.

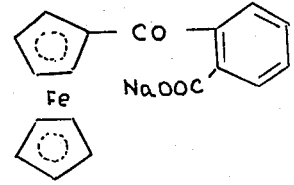

A suspension of aluminum chloride in dry methylene chloride or in higher ethers, e.g. n-dibutyl ether, is added by portions to the reaction mixture, whereupon the latter is heated at a temperature of 40° – 45°C for 4 – 5 hours with stirring. Then the reaction mixture is cooled to 10° – 15°C and cool water acidified with hydrochloric acid is added thereto. Thereupon the organic layer is separated, washed with water and the solvent is distilled off. Sodium hydroxide is added to the resultant residue, viz., the ethyl ester of o-carboxybenzoylferrocene, and the mixture is heated at a temperature in the range of 95° – 98°C:

The reaction mixture is filtered at a temperature of 80°C. for separating the tarry products. The filtrate is cooled and a crystalline salt is separated which is then purified by re-crystallization from the minimum amount of water.

In order to obtain a purer end product, said filtrate can be cooled and then acidified with hydrochloric acid, and o-carboxybenzoylferrocene can be separated and heated with sodium hydroxide to prepare the end product - the sodium salt of o-carboxybenzoylferrocene which is employed as the active ingredient of the proposed medicinal preparation for treating ozena.

The proposed preparation is prescribed in the form of tablets containing from 0.1 to 0.3 g of the active principle ingredient, which are to be taken after or during meals chasing them with water.

The tablets need not be chased by hydrochloric acid, gastric juice, ascorbic acid or other acidic products, which fits the proposed preparation for use by patients suffering from gastro-intestinal diseases such as ulcers, gastritis and the like.

Eight years of application have revealed no contraindications for the use of the proposed preparation.

What is claimed is:

1. A method of treating ozena in a human having said condition which comprises oral administration an effective amount of tablets, each containing from 0.1 to 0.3 g of the sodium salt of o-carboxybenzoylferrocene.

2. The method of claim 1 wherein said tablets are administered 2 to 3 times a day for 20 to 40 days.

* * * * *